United States Patent [19]

Oravecz et al.

[11] Patent Number: 6,020,917

[45] Date of Patent: *Feb. 1, 2000

[54] VIDEO DISPLAY SYSTEM FOR LOCATING A PROJECTED IMAGE ADJACENT A SURGICAL FIELD

[75] Inventors: Michael G. Oravecz, Rochester; Roger G. Greenwald, Holley; Daniel E. McGarry, North Chili; Jude S. Sauer, Pittsford, all of N.Y.

[73] Assignee: Laser Surge, Inc., Rochester, N.Y.

[ * ] Notice: This patent is subject to a terminal disclaimer.

[21] Appl. No.: 08/673,612

[22] Filed: Jun. 25, 1996

Related U.S. Application Data

[63] Continuation of application No. 08/219,492, Mar. 29, 1994, Pat. No. 5,543,832.

[51] Int. Cl.[7] .......................................... H04N 7/18
[52] U.S. Cl. ........................ 348/77; 348/65; 348/744; 359/823; 359/443; 353/50; 600/103
[58] Field of Search .................. 348/45, 65, 77, 348/240, 347, 744, 788, 789, 787; 353/77, 50; 359/443, 822, 823, 829, 507, 513, 448; 600/101, 102, 103, 114; H04N 9/31, 5/71, 7/18

[56] References Cited

U.S. PATENT DOCUMENTS

| | | | |
|---|---|---|---|
| 3,229,570 | 1/1966 | Erban | 353/39 |
| 4,209,807 | 6/1980 | Arita | 348/782 |
| 4,245,256 | 1/1981 | Kokubo et al. | 348/789 |
| 4,479,144 | 10/1984 | Yamazaki et al. | 348/788 |
| 5,101,807 | 4/1992 | Kawashima | 600/112 |
| 5,311,859 | 5/1994 | Monroe | 600/112 |
| 5,543,832 | 8/1996 | Oravecz et al. | 348/65 |

FOREIGN PATENT DOCUMENTS

| | | |
|---|---|---|
| 0 427 358 A1 | 5/1991 | European Pat. Off. . |
| 0 665 686 A2 | 8/1995 | European Pat. Off. . |
| 31 00 607 A1 | 4/1982 | Germany . |

*Primary Examiner*—Michael H. Lee
*Attorney, Agent, or Firm*—Harter, Secrest & Emery LLP; Stephen B. Salai

[57] ABSTRACT

A method and apparatus for projecting an image of a surgical field along an optical path to intersect a display screen which is nonperpendicular to the optical path and adjacent the surgical field. A video projector system and accompanying optics impart at least one of a tilted focal plane or depth of focus to the projected image. The optical path of the projected image is located adjacent the surgical field. A sterilizable display screen is located in the optical path adjacent the surgical field so that a normal to the screen is noncoincident with the optical path and the projected image on the screen is of constant focus across the screen.

8 Claims, 6 Drawing Sheets

VIDEO DISPLAY SYSTEM FOR LOCATING A PROJECTED IMAGE ADJACENT A SURGICAL FIELD

The present application is a continuation in part of U.S. patent application, Ser. No. 08/219,492, filed Mar. 29, 1994 now U.S. Pat. No. 5,543,832 naming Michael Oravecz et al., herein incorporated by reference.

FIELD OF THE INVENTION

The present invention relates to video display systems for displaying a surgical field, and more particularly, to a method and apparatus for projecting an endoscopic image along an optical path and upon a sterilizable screen adjacent the surgical field, wherein the screen is nonperpendicular to the optical path so as to optimize the viewing angle of the projected image.

BACKGROUND OF THE INVENTION

Surgical procedures are often performed in surgical fields which are of a limited size or beneath the skin. With respect to endoscopic procedures, there are several methods for viewing the body interior. For example, the surgeon may look directly through the eyepiece of the endoscope. Alternatively, a beam splitter may be used to provide a second eyepiece for a surgical assistant to simultaneously view the surgical field. For those instances where more than two simultaneous views are necessary, the second view is replaced with a video camera. Splitting the beam between the eyepiece and video camera allows the surgeon to view the surgical field in a high resolution display while the video camera and monitor allow the remaining members of the surgical team to view the procedure. Alternatively, a video camera is mounted directly to the endoscope and one or more monitors are located about the operating environment so that the surgical team may view the field.

Alternatively, liquid crystal display (LCD) monitors can be employed. However, the LCD monitors have a limited viewing angle and an LCD having a sufficient size to permit sufficiently high resolution creates a substantial intrusion to the operating environment. In addition, the LCD monitors are nondisposable, thereby creating a sterilization problem. Further, the accompanying electronics and wires add undesired clutter to the operating environment.

Standard video projection systems are also used. However, the video projecting systems require the screen to be perpendicular to the projection axis. Therefore, locating the display screen at an optimum viewing angle causes a portion of the projected image to be out of focus. Alternatively, the projection path excessively interferes with the operating environment and is subject to frequent interruptions. Further, standard projection screens are irreparably stained by blood and bodily fluids, while disposable flexible screens require stretching or sufficient tension to retain the screens in a proper orientation.

The disadvantages of the prior systems include disorientation created by locating the monitor or projected image of the surgical field remotely from the surgical field. This disorientation is enhanced by the surgeon being unable to view the area of the surgical field and their hands simultaneously. In addition, forcing the surgeon to focus on an image at a relatively large distance while the surgeon's hands are adjacent the body is an unnatural perspective detrimental to the efficiency of surgeons. In addition, constraints on the available locations of the video monitors relative to the surgical field are such that the direction of movement of an instrument within the surgical field is often not translated into a movement in the same direction in the projected image.

Therefore, a need exists for a video display system for an operating environment, wherein a high resolution projected image of a surgical field or other video information may be located adjacent the surgical field and in a viewing orientation which is optimal to the surgeon. In addition, the need exists for a video display system which presents an image which is consistent with the direction of movement within the surgical field. The need also exists for a disposable and/or sterilizable screen for permitting contact with the surgical team, or blood and other bodily fluids during the surgical procedure. The need also exists for a viewing screen which may be located at a favorable viewing angle without jeopardizing the integrity of the projected image.

SUMMARY OF THE INVENTION

The present invention includes a video projection system designed for a sterile operating environment for locating a viewing screen at an optimum viewing angle adjacent a surgical field and within the reach of the viewers. As the screen is adjacent the surgical field and within reach of the surgical field, direct eye and hand coordination is enhanced as viewers can simultaneously view the display of the surgical field and their hands. In addition, communication is facilitated by permitting manual referencing to the images on the view screen to unequivocally identify areas within the surgical field. Locating the projected image adjacent the surgical field also reduces fatigue of the surgeons.

In a preferred embodiment of the invention an endoscopic surgical field is displayed upon a viewing screen adjacent the surgical field. A high resolution small screen projection system having a tilted projection optic (compensator) projects the endoscopic image along an optical path. Mirrors locate the optical path adjacent the surgical field. A disposable/sterilizable viewing screen is retained along the optical path adjacent the surgical field at a predetermined distance from the projector at a nonperpendicular angle to the optical path. The tilted projection optic and angle between the optical path and the normal to the screen provides uniform focus of the entire projected image upon the screen.

In a second embodiment of the invention, a projected image is created to exhibit a depth of focus extending along the optical path. The viewing screen may then be disposed in the optical path with a normal to the screen being nonperpendicular angle to the optical path such that the projected image is of substantially uniform focus across the viewing screen.

DETAILED DESCRIPTION OF THE PREFERRED EMBODIMENTS

Figure 1:
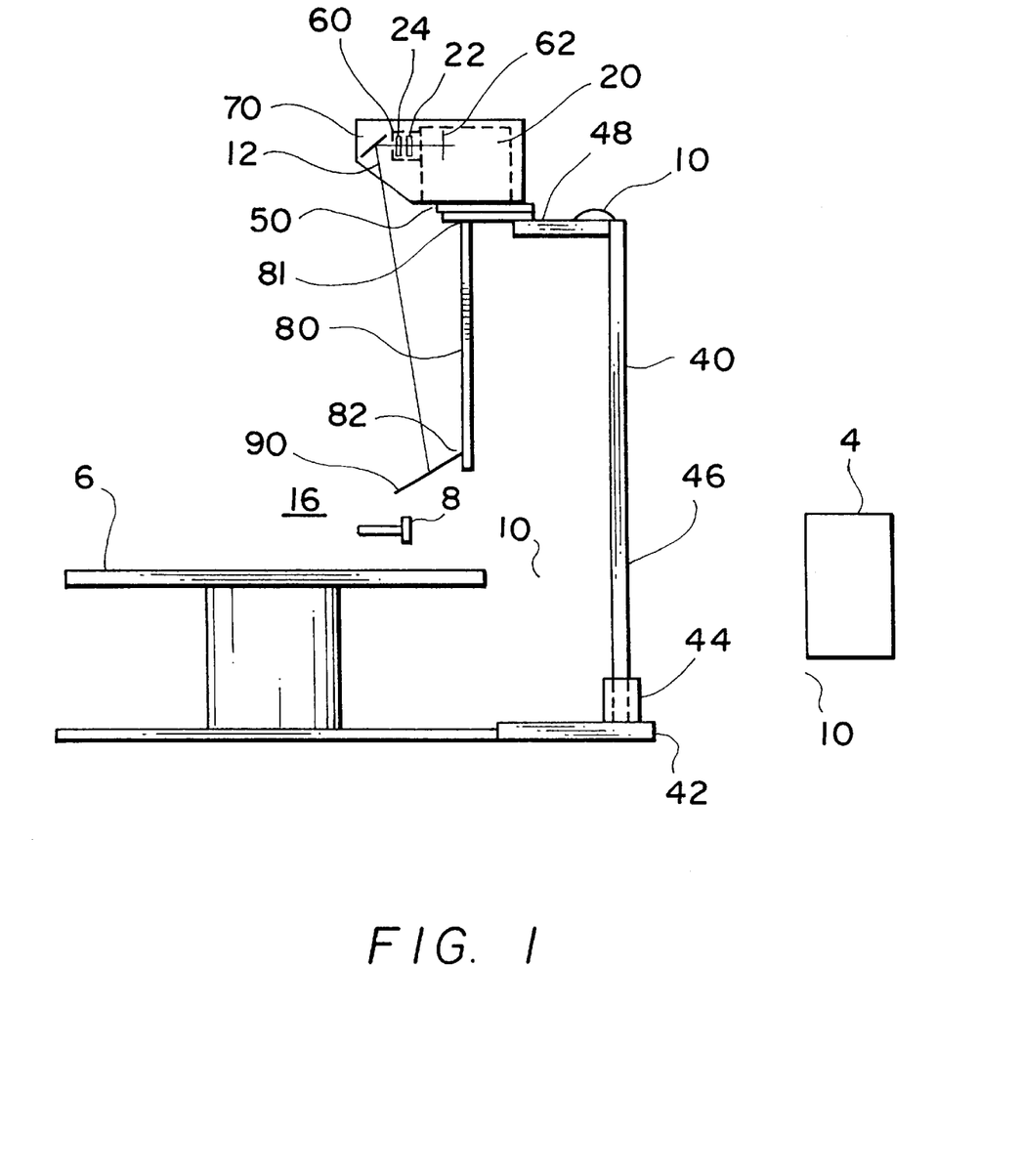
FIG. 1 is a side elevational view of a first embodiment of the present invention.

Referring to FIG. 1, a first embodiment of the present invention is disclosed. A video projector 20 is supported by a stand 40 to be remotely located from an operating table 6 and surgical field 16. The video projector 20 projects an image along an optical path 12, wherein the optical path passes through a tilted projection optic 60 (compensator) and intersects a disposable/sterilizable screen 90. An image gathering system 8, such as an endoscope, as well known in the art is used to gather the image to be projected by the projector 20. The image gathering system 8 is operably connected to the projector 20 via an image gathering system electronic converter 4, as known in the art by a standard transmission line 10, such as a video cable.

The video projector 20 is a self-contained system which projects a high quality high resolution video image along the optical path 12. Preferably, the projector 20 has a resolution which is substantially equal to a surgical video monitor. The projected resolution is approximately 450×245 pixels (horizontal by vertical). The video projector 20 may be any of a commercial available types such as the LC300 manufactured by Eiki.

In this embodiment the tilted projection optic 60 (compensator) includes the standard focusing, zoom optics 22 of the video projector 20 and a diopter lens 24. The diopter lens 24 is any of a variety well known in the art, such as the Professional Ser. 9 Plus ½ lens manufactured by Tiffen. The diopter lens 24 is used to change the focusing range of the focusing, zoom optics 22 of the projector 20 to the nearer distances. The focusing, zoom optics 22 are adjusted to produce an image the size of the viewing screen 90 at a practical projection length. The focusing, zoom optics 22 are also adjusted to focus the image onto the viewing screen 90. The projection length along the optical path 12 is sufficiently long to position the projector 20 well above or removed from the operating table 6 and out of the way of personnel and equipment. Preferably, the projection optic 60 and projector 20 location are selected to provide an optimum image size at the point the optical path 12 is adjacent the surgical field 16. For example in general surgery, these selections would provide a projected image that is approximately life size.

The video projector 20 may be mounted horizontally or vertically. As shown in FIG. 1, in the horizontal mount of the projector, the stand 40 is used to support the projector 20. The stand 40 includes a base 42 having a connected post support 44. A post 46 extends from the post support 44 to terminate a distance above the operating table 6. An articulated arm 48 is connected to the post 46 to horizontally locate the video projector 20. Preferably, the video projector 20 is mounted to a base plate 50 which in turn is mounted to the articulated arm 48. Power and video cables 10 may extend within the post 46 and articulated arm 48 to the projector 20.

Figure 5:
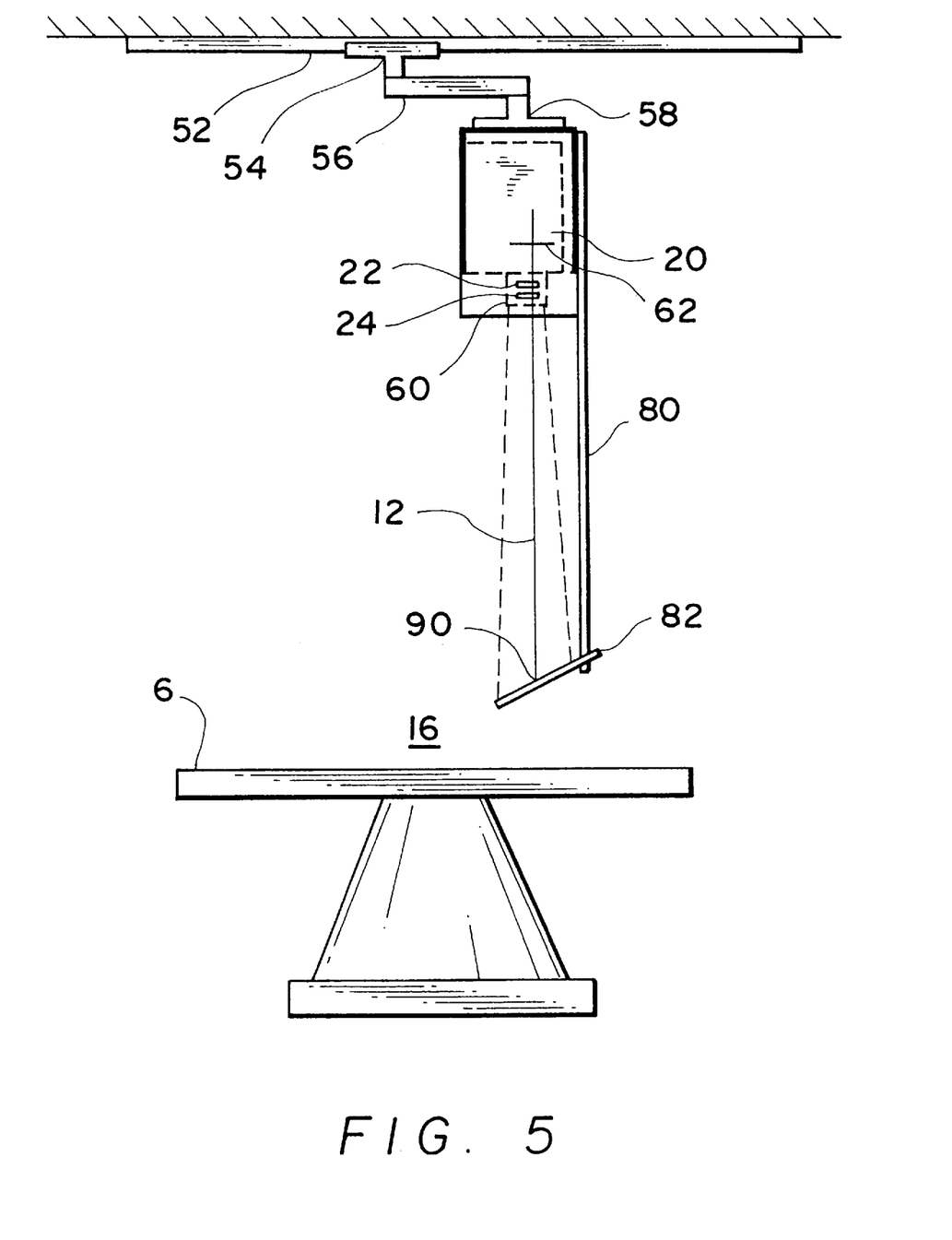
FIG. 5 is a side elevational view of a second embodiment of the invention.
Figure 6:
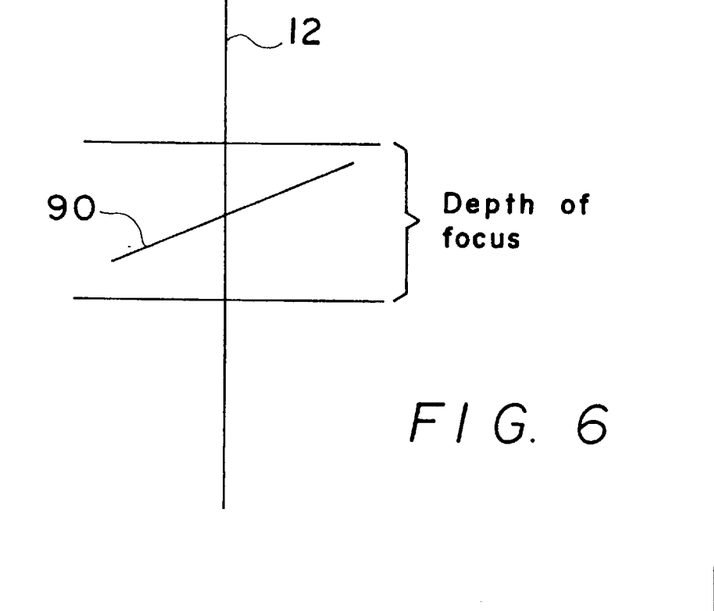
FIG. 6 is a schematic view showing a depth of focus along the optical path.
Figure 7:
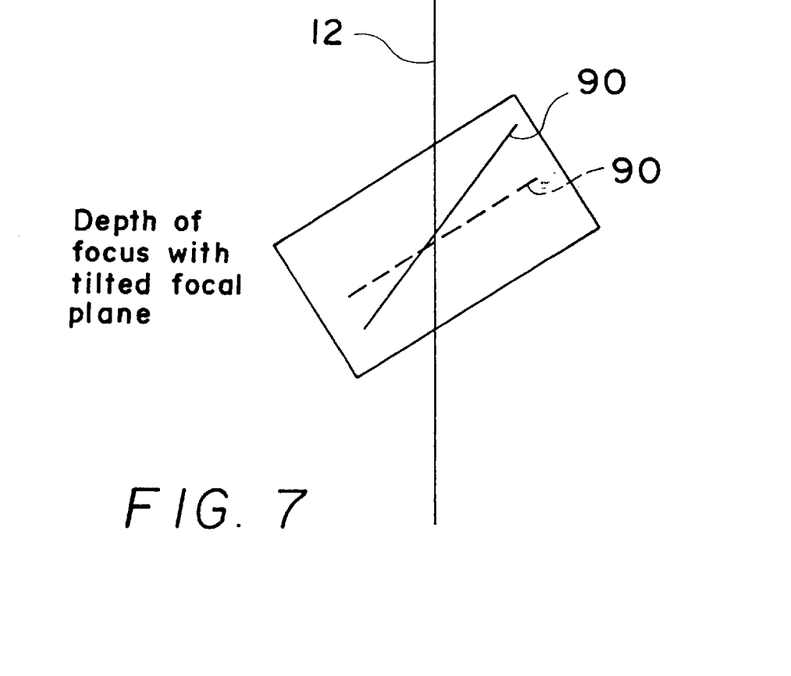
FIG. 7 is a schematic view showing a viewing screen having a normal noncoincident to the adjacent optical path disposed within the projected depth of focus along the optical path.

Alternatively as shown in FIG. 5, the vertical mounting of the projector 20 includes a linear track 52 affixed to the ceiling, wherein the track retains an arm mount 54. A counter balanced arm 56 extends from the arm mount 54 to horizontally displace the projector 20. A projector support 58 is connected to the arm mount 54 to operably retain the video projector 20 in a vertically projecting orientation.

Projection Lens

As shown in FIG. 1, the optical path 12 passes through an object plane 62 and the projection optic 60 and extends to the viewing screen 90. As previously stated, the optimal orientation of the viewing screen 90 and location of the video projector 20 results in the viewing screen being nonperpendicular to the optical path 12. That is, the normal of the screen 90 is set at an angle with respect to the optical path 12. In order to obtain a focused image across the entire angled screen 90, the projection optic 60 makes the object plane 62 conjugate to the screen surface 90. In conventional projection systems, the conjugate object and image planes are nominally perpendicular to the optical axis of the projection optic. In contrast in this embodiment, these planes are tilted relative to the optical axis of the projection optic 60, so that upon projection on the off angle screen 90, the entire image is in focus.

To minimize interference in the operating room and reduce interruption of the projected image, the optical path 12 adjacent the surgical field 16 is substantially vertical and does not include a substantial horizontal component which would interfere with a larger portion of the operating field. Therefore, the foot print of the optical path 12 is substantially minimized. In the embodiments of FIGS. 1 and 5, the adjacent portion of the optical path lies within the foot print of the viewing screen. That is, the viewing screen overlies a certain horizontal area and the adjacent portion of the optical path is within the vertical projection of the horizontal area.

As shown in FIG. 1, a mirror 70 directs the optical path 12 from the projection optic 60 downward to viewing screen 90. Although only one mirror 70 is shown, a series of mirrors may be used to locate the optical path 12 relative to the surgical field 16.

Referring to FIG. 1, a screen rod 80 depends from the projector base plate 50 and terminates adjacent the operating table 6 and surgical field 16. The screen 90 is affixed to the rod 80 to be located at a predetermined distance from the projector 20. As the rod 80 is mounted upon the articulated arm 48, horizontal location of the screen 90 may be adjusted. The rod 80 is rigidly affixed relative to the projector 20 by threaded fasteners, as well known in the art.

Viewing Screen

The viewing screen 90 is a lightweight compact screen made from a PVC sheet material. Preferably, the optical surface of the screen 90 has a matte white finish. The PVC screen material is not distorted or permanently stained by blood or other bodily fluids. That is, the screen 90 may be easily rinsed with sterile saline or water and dried with sterile gauze to quickly remove any foreign matter which distorts the projected image.

Figure 2:
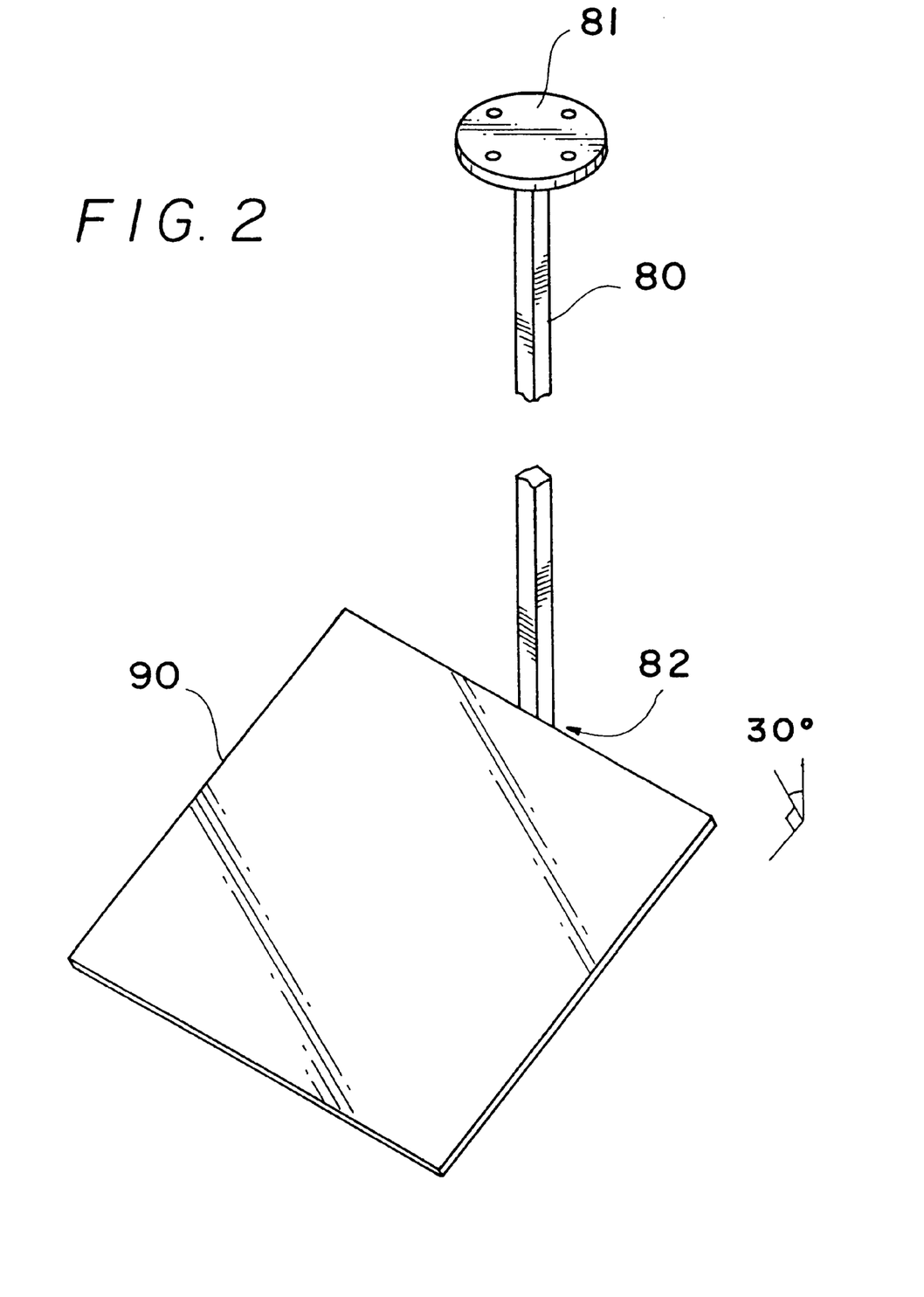
FIG. 2 is a broken perspective view of the viewing screen.

The viewing screen material has a minimal internal light transmission and scattering. The screen material is rigid and light weight so that only a thin sheet is required to maintain a self supporting planar surface. The viewing screen has the same dimension as a typical video monitor, approximately a 13 inch diagonal. The normal to screen 90 is preferably mounted at an approximately 30° angle from a vertical position, as shown in FIG. 2. Therefore, the vertical size of the screen 90 is longer than the standard 4 to 3 video aspect ratio. However, as dictated by the operating environment, the screen 90 may be from approximately 15° to 85° from a vertical position. As the optical path 12 is substantially vertical in the area of the surgical field 16, the orientation of the viewing screen 90 in a nonhorizontal position provides that the viewing screen is nonperpendicular to the optical path.

Screen Mounting System

The screen mounting system includes the screen mount 82 connected to the rod 80 and a fixture or cooperating structure on the back of the screen 90.

The rod 80 is substantially rigid to eliminate vibration of the screen 90 relative to the video projector 20. In addition, there is at least some adjustability between the video projector 20 and the rod 80 to correct for minor misalignments. The adjustment includes both vertical and horizontal components. However, the horizontal range of motion is relatively small compared to the range of motion of the post 46 and articulated arm 48.

Figures 3A, 3B:
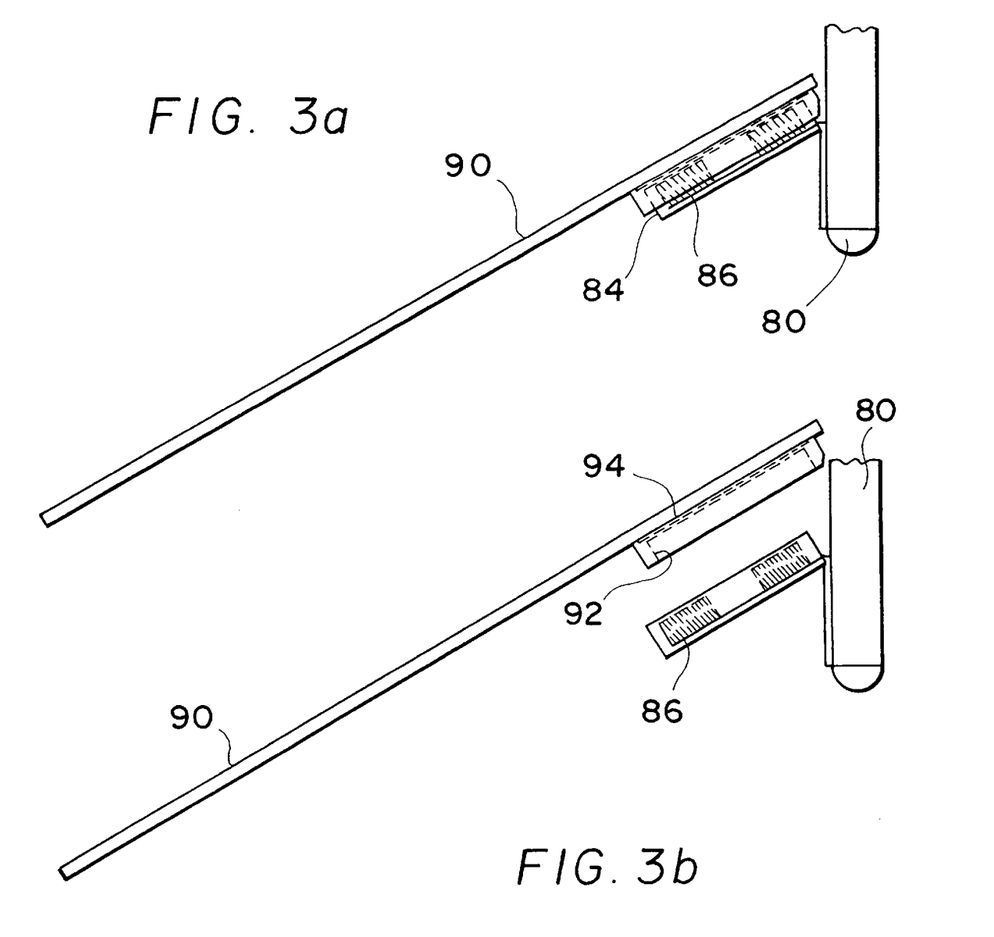
FIGS. 3a and 3b are side elevational views of the first embodiment of attaching the viewing screen to a rod.

In the first embodiment, as shown in FIGS. 3a and 3b, the screen mount 82 includes a magnetic socket mechanism 84. A plastic encapsulated rectangular magnet 86 is mounted onto the rod 80 and is inclined to the optimal viewing position. The viewing screen 90 includes a socket 92 having a corresponding periphery, wherein the socket includes an embedded layer of steel or other magnetically active material 94. The rectangular shape of the encapsulated magnet 86 matches the shape of the socket 92 so that the screen 90 is easily and accurately placed in the optimal viewing position. The attraction between the magnet 86 and the steel is sufficient to retain the screen 90 in operable position. However, the magnetic attraction is sufficiently small so that if the patient inadvertently contacts the screen 90, the screen with readily disengage to prevent injury.

Figures 4A, 4B:
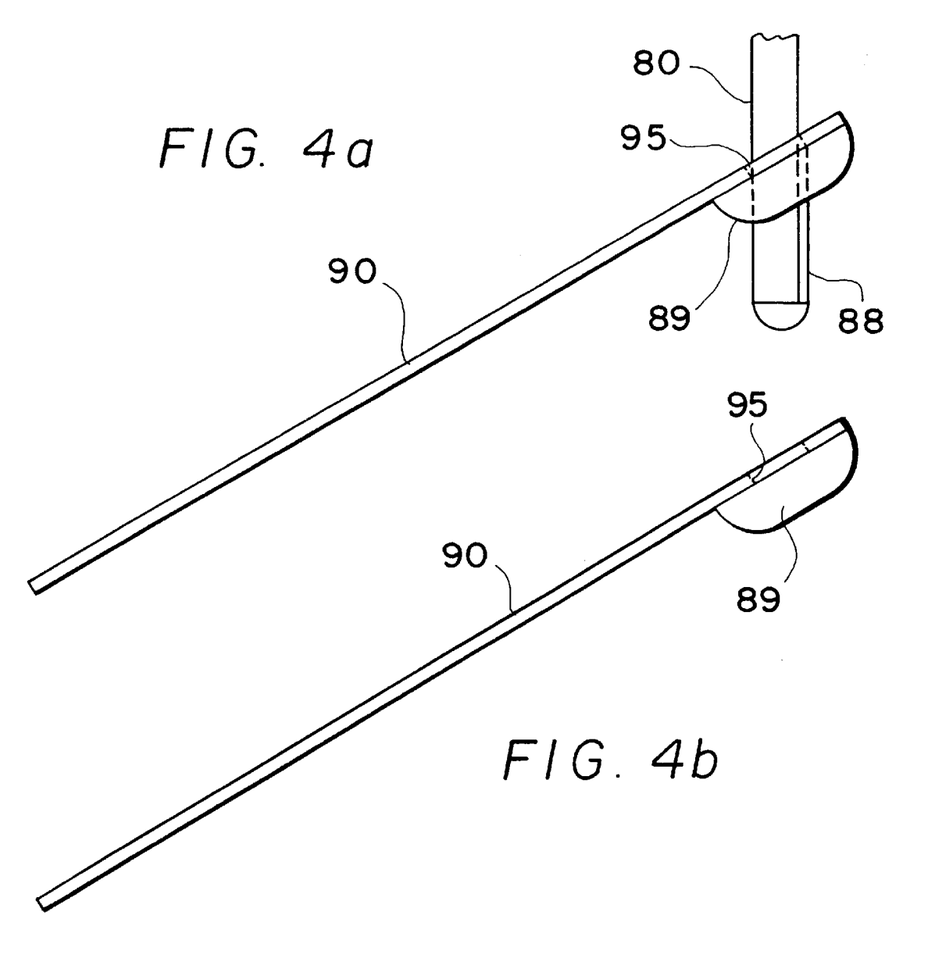
FIGS. 4a and 4b are side elevational views of an alternative attachment of the viewing screen to the mount.

Alternatively, the screen 90 may include spring biased members or a pocket, recess or flange which cooperatively mates with a corresponding structure on the screen mount 82 to releasably and operatively retain the screen relative to the rod 80. In the second preferred embodiment of the screen mount shown in FIGS. 4a and 4b, the screen 90 includes an aperture 95 and depending stabilizing flanges 89 which mate with a screen mount stop 88 on the rod 80.

Operation

Although the present invention is described in terms of endoscopic and laparoscopic surgery, the invention is applicable to any procedure where it is useful to display information adjacent the viewer and the surgical field. The information can be displayed in a video format and include x-rays, ultrasonic or topographic images and vital signs information.

As employed for endoscopic surgery, the location, height and orientation of the viewing screen 90 are preferably set for the surgical team prior to surgery. The articulating arm 48 or adjusting track 52 and counterbalanced arm 56 permit locating the viewing screen 90 horizontally and adjusting the vertical control in arm 48 or arm 56 permits the desired orientation of the viewing screen 90. Preferably, the viewing screen 90 is oriented so that the direction of motion in the projected image on the screen 90 directly corresponds to the direction of motion in the surgical field 16. In addition, the viewing screen 90 is located within arms length (approximately three feet) of the surgical field 16 and below eye level of the viewer. While the viewing screen 90 is optimally located adjacent to and at the same vertical elevation as the surgical field 16, the viewing screen may be intermediate the surgical field and eye level of the viewer. In addition, the viewing screen 90 is sufficiently near the surgical field so that a surgeon working in the surgical field which is projected upon the viewing screen 90 can readily contact the viewing screen to identify a portion of the surgical field.

An active video signal and standard AC electrical power inputs are connected to the video projector 20 from the gathering system 8 and converter 4. The active video signal may come from the endoscope or an other image generating mechanism trained on a portion of the surgical field 16. The video projector 20 transfers the electrical video signal into an optical image and projects the optical image along the optical path 12 to the projection optic 60. The image size and focus are set by the details of the projection optic 60 so that they match the viewing screen size and location. Any observed keystoning, a trapezoidal shaping of the image caused by the tilt of the viewing screen relative to the optical path, is corrected at installation by an electronic adjustment of the video projector 20. Alternatively, keystoning can be corrected in the projection optic 60 by including anti-keystoning optical design principles well known in the art.

The tilt of the viewing screen relative to the optical path also causes a unidirectional enlargement of the projected image that results in an observed modification of the image's aspect ratio. Fundamentally, this enlargement is a function of the inverse cosine of the angle between the screen normal and the optical path. This enlargement effect is partially self-correcting due to the expansion of the beam as a function of distance from the projector. For tilt angles less than about 30° the effect on the observed aspect ratio is negligible (less than 10%). For larger tilt angles and for precision applications, a unidirectional image magnification compensation can be accomplished electronically or optically. The optical methods include an anamorphic prism pair, a cylindrical lens telescope, or decentration of a tilted projection lens.

The present invention is directed to a viewing screen which may be appropriately positioned and angled within a sterile, surgical field to provide convenience and image quality necessary for successful surgical procedures.

The unique restrictive conditions found in a surgical setting require that a viewing or display system satisfy the conditions that:

1. Neither the surgeon, the surgical instruments nor the surrounding operating room equipment should interfere with or compromise the function of the display system;
2. Complex electronics and unnecessary hardware should not be introduced into the sterile surgical environment;
3. The size and weight of anything introduced into the surgical field should be no greater than as required by the useful function; and
4. Blood and other surgical fluids must not seriously impair the function of the display system.

The present use of a video projector physically separates the viewing screen (projected image) from the illumination hardware, illumination electronics, video processing electronics, the display power electronics, the image transmission line (connected to the image gathering system) and the display power cable. Further, the use of video projector technology allows the image to be viewed with a light weight screen that may be formed of materials resistant to blood and surgical fluids. To additionally achieve: (1) the required clarity in the displayed image, (2) a viewing screen convenient to the surgeons, and (3) flexibility in the projector's mounting configuration and orientation with respect to the surgical field, it has been found by the present inventors that this requires the depth of focus and the tilt of the focal plane of the projected image relative to the optical axis to be appropriately manipulated. The manipulation of the depth of field and the angle of the focal plane with respect to the optical axis is done so that the projected image displayed on the viewing screen has a substantially uniform focus across the screen and its resolution is not limited by defocusing, while image brightness is maximized.

The concept of depth of focus rests on the assumption that for a given optical system, there exists a blur (due to defocusing) of small enough size such that it will not adversely affect the usefulness of the system. The depth of focus is the amount by which the image may be shifted longitudinally with respect to some reference plane and introduce no more than the acceptable blur. That is, the depth of focus is defined by the amount by which any point in the image (any point on the viewing screen) may be shifted along the optical axis with respect to the video projector and will deliver an image that is substantially free from unacceptable defocusing blur. The video projector depth of focus is based on the concept that a defocused blur which is smaller than a pixel in the image is not substantially noticeable. The image pixels are determined by the image generating device in the video projector (for example the LCD panels in an LCD video projector).

There is a volume of space, the focal volume, defined by the size of the projected image at the focal plane and by the video projector depth of focus on either side of the focal plane. The focal plane is a plane of "best" focus for the system. Within the focal volume, sufficient image clarity (defocus blur smaller than pixel size) and a convenient viewing screen angle can both be achieved.

At one extreme, the focal volume is relatively small and substantially planar, or plate like. When the focal volume is plate like and the viewing screen relative to the optical axis is substantial, for example 30 degrees, the focal plane must be tilted relative to the optical axis in such a way that the focal plane is substantially parallel to and in the same location as the tilted viewing screen. Thus, the viewing screen surface falls completely within the focal volume. A plate like focal plane that is tilted relative to the optical axis is realized by disposing a projection lens, having a relatively large clear aperture, in the optical path so that the projected image passes through the projection lens and so that the projection lens has an optical axis tilted with respect to the optical path. This provides for a relatively bright and focused image across the viewing screen.

In another extreme, the focal volume is large and slab like. The focal volume is thick enough (extends sufficiently along the optical path) that the viewing screen may be disposed entirely within the focal volume even if the focal plane and the viewing screen surface are not substantially parallel to each other. A slab like focal plane is realized by disposing a projection lens, having a relatively small clear aperture, in the optical path so that the projected image passes through the projection lens. If there are no tilting projection optics employed, then the normal to the focal plane is parallel to the optical axis, yet, the normal to the viewing screen may be disposed approximately 30 degrees from the optical axis while maintaining a projected image clarity of acceptable defocused blur.

Between these two extreme configurations, a combination of many factors will dictate the desired compromise of the focal plane tilt and depth of focus. These factors include video projector mounting configuration, screen angle, image size, image resolution (number of pixels), distance between the screen and the projector, optical aberrations, the size and numerical aperture of the projector's image generating device and the desired or required projected image brightness.

While a preferred embodiment of the invention has been shown and described with particularity, it will be appreciated that various changes and modifications may suggest themselves to one having ordinary skill in the art upon being apprised of the present invention. It is intended to encompass all such changes and modifications as fall within the scope and spirit of the appended claims.

What is claimed:

1. A video display system for projecting an image of an endoscopic surgical field upon a screen in a sterile environment adjacent the surgical field so that an operator may simultaneously view the projected image surgical field and the surgical field, comprising:

(a) an image gathering system for gathering the image of the surgical field;

(b) a video projector operably connected to the image gathering system for projecting the image along an optical path, the image having a depth of focus extending along the optical path;

(c) a projection optic disposed in the optical path so that the projected image passes through the projection optic, the projection optic having an optical axis tilted with respect to the optical path for tilting the projected image to dispose a focal plane non perpendicular to the optical path; and (d) a viewing screen intersecting the optical path, wherein a normal to the viewing screen is movable relative to the optical path between a parallel and a nonparallel intersecting orientation defining an offset angle;

the offset angle and one of the non perpendicular focal plane and the depth of focus, selected so that the projected image displayed on the viewing screen has a substantially uniform focus across the viewing screen.

2. A video display system for a sterile environment for locating a projected image of a surgical field on a screen at a predetermined location adjacent the surgical field, comprising:

(a) an image gathering system for gathering an image of at least a portion of the surgical field;

(b) a video projector operably connected to the image gathering system for projecting the image along an optical path, the projected image having a depth of focus extending along the optical path; and (c) a viewing screen having a substantially planar viewing surface, wherein a normal to the viewing surface is nonparallel to the optical path adjacent the viewing screen at a sufficient angle for disposing the viewing screen within the given depth of focus so that the image being projected upon the viewing screen is of substantially constant focus.

3. The video display system of claim 2, further comprising a mounting member connected to the viewing screen to operably retain the viewing screen relative to the optical path at a predetermined distance from the projector and adjacent the surgical field at a sufficient angle to dispose substantially the entire viewing screen within the depth of field.

4. The video display system of claim 2, wherein the video projector and the viewing screen are a front projection pair, the viewing screen having a vertical foot print which contains an adjacent portion of the optical path.

5. The video display system of claim 2, wherein the video projector and the viewing screen are a rear projection pair.

6. The video display system of claim 2, wherein the aspect ratio of the displayed image is substantially equal to the aspect ratio of the image gathering system.

7. The video display system of claim 6, wherein the aspect ratio of the displayed image is achieved by one of decentration of a tilted projection lens, an anamorphic prism pair and a cylindrical lens telescope.

8. A video display system for projecting visual information upon a screen in a sterile environment adjacent a surgical field, comprising:

(a) an image gathering system for gathering an image of the surgical field;

(b) a video transmission line connected to the image gathering system;

(c) a video projector connected to the video transmission line for projecting the image along an optical path and creating a depth of focus of the projected image extending along the optical path; and (e) a viewing screen spaced from the projector and intersecting the optical path, wherein a normal to the screen is nonparallel to the intersecting optical path for disposing the depth of focus across the viewing screen and produce a projected image having a substantially uniform focus throughout the entire image.

* * * * *